(12) United States Patent
Chen et al.

(10) Patent No.: US 6,939,536 B2
(45) Date of Patent: *Sep. 6, 2005

(54) COSMETIC COMPOSITIONS CONTAINING WATER-SOLUBLE POLYMER COMPLEXES

(75) Inventors: Shih-Ruey T. Chen, Pittsburgh, PA (US); Valentino L. DeVito, Pittsburgh, PA (US); Kevin W. Frederick, Evans City, PA (US)

(73) Assignee: WSP Chemicals & Technology, LLC, Ambridge, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/122,750

(22) Filed: Apr. 15, 2002

(65) Prior Publication Data

US 2003/0064044 A1 Apr. 3, 2003

Related U.S. Application Data

(60) Provisional application No. 60/284,043, filed on Apr. 16, 2001.

(51) Int. Cl.$^7$ .............................. A61K 7/06; A61K 6/00; C08G 63/48; C08L 1/00
(52) U.S. Cl. .................... 424/70.1; 424/70.13; 424/401; 525/54.21; 525/54.24; 524/35; 524/47; 524/17; 524/25; 524/27
(58) Field of Search .............................. 424/70.1, 70.13, 424/78.1, 78.12, 401, 70, 71; 524/35, 47, 17, 25, 27; 525/54.21, 54.24

(56) References Cited

U.S. PATENT DOCUMENTS

| | | | |
|---|---|---|---|
| 3,770,673 A | 11/1973 | Slagel et al. ................. | 527/312 |
| 3,891,580 A | * 6/1975 | Morris et al. | |
| 3,986,825 A | 10/1976 | Sokol ............................ | 8/406 |
| 4,028,290 A | 6/1977 | Reid ........................... | 524/768 |
| 4,105,605 A | 8/1978 | Cottrell et al. ............... | 528/487 |
| 4,175,572 A | 11/1979 | Hsiung et al. ............... | 132/204 |
| 4,464,523 A | 8/1984 | Neigel et al. ................ | 527/300 |
| 4,703,801 A | 11/1987 | Fry et al. ..................... | 166/293 |
| 4,923,694 A | 5/1990 | Shih et al. .................... | 424/70 |
| 5,275,809 A | 1/1994 | Chen et al. ................... | 424/70 |
| 5,296,218 A | 3/1994 | Chen et al. ................... | 424/70 |
| 5,575,924 A | * 11/1996 | Bair et al. | |
| 5,609,862 A | 3/1997 | Chen et al. ............... | 424/70.11 |
| 5,644,049 A | 7/1997 | Guisti et al. .................. | 536/53 |
| 5,658,993 A | * 8/1997 | Denzinger et al. | |
| 5,693,034 A | 12/1997 | Buscemi et al. ............ | 604/265 |
| 5,803,071 A | 9/1998 | Iovine et al. ................. | 427/70 |
| 5,879,670 A | 3/1999 | Melby et al. ............ | 424/70.16 |
| 5,925,379 A | 7/1999 | Mandeville, III et al. ... | 424/484 |
| 6,066,315 A | 5/2000 | Melby et al. ............ | 424/70.16 |
| 6,110,451 A | 8/2000 | Matz et al. ............... | 424/70.16 |

FOREIGN PATENT DOCUMENTS

| | | |
|---|---|---|
| EP | 0308189 | 3/1989 |
| EP | 0308190 | 3/1989 |
| GB | 2113245 | 8/1983 |

* cited by examiner

Primary Examiner—Shaojia Anna Jiang
(74) Attorney, Agent, or Firm—Blynn L. Shideler; Krisanne Shideler; BLK Law Group

(57) ABSTRACT

A composition for treating a keratin based substrate that includes a cosmetically acceptable medium containing a water-soluble interjacent complex. The water-soluble interjacent complex includes a first water-soluble polymer and a second water-soluble polymer formed by polymerizing one or more water-soluble monomers in the presence of the first water-soluble polymer. The water-soluble interjacent complex is characterized in that it forms a solution in water that is free of insoluble polymer particles. The water-soluble interjacent complex is used in a method of treating a keratin based substrate, whereby a cosmetically acceptable medium is applied to the substrate and contains from 0.1–20% by weight of the water-soluble interjacent complex.

27 Claims, No Drawings

COSMETIC COMPOSITIONS CONTAINING WATER-SOLUBLE POLYMER COMPLEXES

CROSS-REFERENCE TO RELATED APPLICATION

This application claims the benefit of U.S. Provisional Patent Application Ser. No. 60/284,043, filed Apr. 16, 2001, and entitled "Water Soluble Polymer Complexes," which is herein incorporated by reference.

BACKGROUND OF THE INVENTION

1. Field of the Invention

The present invention relates to novel cosmetically acceptable compositions containing a cosmetically acceptable medium that includes polymer compositions and methods for treating keratin. The cosmetically acceptable medium can be a hair or skin care product, such as a shampoo, conditioner, shower gel, bar soap, styling product, or rinse, or a skin care product, such as a cleanser, lotion, or cream.

2. Brief Description of the Prior Art

The surface properties of keratin are of interest in cosmetic science, and there has been a long-standing desire to discover ingredients, which will beneficially affect the topical and bulk condition of keratinous substrates, such as hair and skin. For example, such ingredients must have adequate adherent properties, so that they are not only adsorbed initially, but are also retained on exposure to water. This property is referred to as "substantivity," i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2–4.0. Therefore, at the pH of a typical shampoo, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos (or to skin care products, such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant: cationic polymer, where the complex is least water-soluble. Generally, cationic conditioners exhibit some incompatibility at these ratios. Compatibility gives a commercially more desirable clear formulation, while incompatibility leads to a haze or precipitation, which is aesthetically less desirable in some formulations.

Hair fixative properties, such as curl retention, are believed to be directly related to film-forming properties of cationic polymers, as well as to molecular weight, with performance generally increasing with increasing molecular weight. However, the fixative properties conferred by cationic polymers generally tend to have a reciprocal relationship to other conditioning properties, i.e., good curl retention usually means that properties, such as wet compatibility, will suffer, and vice versa.

Keratin conditioning additives generally are of three primary types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylaminoethylmethacrylate, and amino functional polydimethylsiloxane. Hydrolyzed animal protein has been frequently used as a keratin conditioner. Also used are natural products, such as collagen and casein. Suitable quaternary ammonium compounds include such products as stearyl dimethyl ammonium chloride.

Generally, two broad areas of skin care products have been recognized as skin conditioners: emollients and humectants. Emollients generally provide improved moisture retention in the skin and plasticization/softening of the skin. Common commercial emollients are mineral oil; petrolatum; aliphatic alcohols, such as stearyl alcohol; lanolin and its derivatives; glycol stearate; and fatty acids, such as triethanolamine oleate. Humectants generally attract moisture, retard evaporation of water from the skin surface, and plasticize/soften skin. Common commercial humectants include glycerin, propylene glycol, sorbitols, and polyethylene glycols.

A desirable skin conditioner should impart at least some of the attributes of an emollient or a humectant, as well as provide improved lubricity and feel to the skin after treatment and/or reduce skin irritation caused by other components in the conditioner, such as, for example, soaps, detergents, foam boosters, surfactants, and perfumes. It is known by those skilled in the art that cationic polymers may be employed as skin and nail conditioners.

At times, it is also desirable that the ingredients of skin and nail care products have adequate adherent properties, so that they are not only adsorbed initially, but are also retained on exposure to water. This property, as in hair care applications, is referred to as "substantivity," i.e., the ability of a material contacted with the keratin of skin or nails to resist removal by water rinse-off. Generally, pH's typical of use conditions, skin, and nails carry a net negative charge. Consequently, cationic polymers have long been used as conditioners in nail and skin care formulations. The substantivity of the cationic polymers for negatively charged skin and nails leads to film formation that facilitates lubricity, moisturizing, and feel.

The skin and nail conditioning properties of lubricity, moisturizing, and feel, are related to the film-forming properties of the cationic polymers, as well as to molecular weight, with performance generally increasing with increasing molecular weight.

Conditioning additives comprising copolymers of dimethyldiallylammonium chloride and other monomers are well known; see, e.g., European Patent No. EP 308189 to Jordan et al. (with acrylamide), European Patent No. EP 0 308 190 to Winkler et al., and U.S. Pat. No. 4,803,071 to Iovine et al. (with hydroxyethyl cellulose). Amphoteric betaines have also been employed in cosmetic compositions; see Great Britain Patent No. GB 2,113,245 to Grollier et al., which discloses use of betainized dialkylaminoalkyl(meth) acrylate together with a cationic polymer.

The use of polymers of diallyldimethylammonium chloride (DADMAC) in the treatment of keratin is also known. See, e.g., U.S. Pat. No. 4,175,572 to Hsiung et al. and U.S. Pat No. 3,986,825 to Sokol. U.S. Pat. No. 5,296,218 to Chen et al. discloses DADMAC-based ampholyte terpolymers containing acrylamide for hair care applications, while U.S.

Pat. No. 5,275,809 to Chen et al. discloses DADMAC-based ampholyte terpolymers containing acrylamidomethylpropyl sulfonic acid for hair care uses.

U.S. Pat. No. 4,923,694 to Shih et al. discloses copolymers of vinyl pyrrolidone and (meth)acrylic cationic monomers that are useful for treating hair. These polymers are able to provide good hair styling properties at low concentrations of cationic monomer, but provide limited substantivity due to their relatively low cationic charge density. When the cationic charge density is increased, the polymers disclosed by Shih et al. become difficult to formulate with due to their decreasing compatibility with anionic surfactants.

U.S. Pat. No. 5,609,862 to Chen et al. discloses hair conditioning polymers comprised of acrylamide, acrylic acid, and a cationic monomer. The conditioning polymers disclosed by Chen et al. are very compatible with anionic surfactants but demonstrate poor compatibility with amphoteric and cationic surfactants. Further, the conditioning polymers of Chen et al. provide poor hair styling properties and only minor conditioning benefit to hair.

U.S. Pat. Nos. 5,879,670 and 6,066,315 to Melby et al. disclose conditioning polymers that include acrylic acid or acrylamidomethylpropanesulfonic acid monomers, (meth)acrylamidopropyl trimethyl ammonium chloride cationic monomers, and (meth)acrylate ester nonionic monomers. The conditioning polymers of Melby et al. are difficult to formulate at low pH and do not provide good hair styling properties.

U.S. Pat. No. 6,110,451 to Matz et al. discloses synergistic combinations of cationic and ampholytic polymers for cleansing and/or conditioning keratin based substrates. The compositions disclosed are often not stable, as strongly cationic polymers tend to form insoluble polymer-polymer complexes and cause the cleansing or conditioning formulation to become hazy, or the polymer-polymer complex precipitates altogether.

Interpenetrating polymer networks (IPN) are intimate combinations of two polymers. The IPN can be in network form, where at least one polymer is synthesized in the immediate presence of the other. In an IPN, at least one of the two polymers is crosslinked and the other may be a linear polymer (not crosslinked). The term IPN has been variously used to describe materials where the two polymers in the mixture are not necessarily bound together, but the components are physically associated.

U.S. Pat. No. 5,925,379 to Mandeville, III et al. discloses a method for removing bile salts from a patient where a polymer network composition, which includes a cationic polymer is administered to the patient. The polymer network composition can include an interpenetrating polymer network, where each polymer within the network is crosslinked or an interpenetrating polymer network, where at least one polymer within the network is not crosslinked. Crosslinking the polymers renders the polymers non-adsorbable and stable. The polymer network composition does not dissolve or otherwise decompose to form potentially harmful byproducts and remains substantially intact so that it can transport ions out of the body following binding of bile acids.

U.S. Pat. No. 5,693,034 to Buscemi et al. discloses an angioplasty catheter that includes a composition coating on a distal end. The coating composition includes the reaction product of vinyl monomers polymerized to form a crosslinked polymer that adheres to the surface of the device in the presence of an uncrosslinked, linear, water-soluble, hydrophilic hydrogel.

U.S. Pat. No. 5,644,049 to Giusti et al. discloses a biomaterial that includes an IPN. The IPN includes an acidic polysaccharide, such as hyaluronic acid and a non-toxic, non-carcinogenic synthetic polymer. The synthetic polymer may be crosslinked or grafted onto the acidic polysaccharide. The crosslinking or grafting is achieved using compounds capable of generating radicals or via functional groups on the acidic polysaccharide and the synthetic chemical polymer.

As the IPN examples described above illustrate, an IPN includes at least one crosslinked polymer with one or more other polymers, which may or may not be crosslinked in intimate combination with each other. When water-soluble polymers are included in the IPN, the resulting IPN is water dispersible, but it does not dissolve in water. While the use of an IPN may provide useful combinations of properties, its water insolubility can be a detriment in cosmetic compositions for treating keratin based substrates.

U.S. Pat. No. 4,028,290 to Reid discloses a complex mixture of crosslinked grafted polysaccharide and acrylamide copolymers that have increased water-absorbing and binding capacity. The copolymers are prepared by reacting a polysaccharide, such as cellulose or starch, acrylamide using a bisulfite-persulfate-ferrous ammonium sulfate grafting initiator.

U.S. Pat. No. 4,703,801 to Fry et al. discloses a graft polymer that has a backbone derived from lignin, lignite, derivatized cellulose, or synthetic polymers, such as polyvinyl alcohol, polyethylene oxide, polypropylene oxide and polyethyleneimine, and pendant grafted groups that include homopolymers and copolymers of 2-acrylamido-2-methylpropanesulfonic acid, acrylonitrile, N,N-dimethylacrylamide, acrylic acid, N,N-dialkylaminoethylmethacrylate, and their salts. The graft copolymers are prepared by reacting the backbone polymer with ceric salts and a persulfate-besulfite redox system in the presence of the selected monomers. The graft copolymers are useful in cementing compositions for use in oil, gas, water and other well cementing operations and impart improved fluid loss capabilities.

U.S. Pat. No. 4,464,523 to Neigel et al. discloses graft copolymers of cellulose derivatives and N,N-diallyl,N-N-dialkyl ammonium chlorides or bromides, prepared using a dry or substantially solvent-free system. The preparation includes impregnating a concentrated aqueous solution of the N,N-diallyl-N,N-dialkyl ammonium halide, water-soluble surfactant, and redox catalyst onto the dry cellulose substrate, heating the reaction mass for sufficient time to achieve polymerization and then drying.

As described above, graft copolymers of polysaccharide and cellulosic backbone polymers are generally prepared by reacting portions of the backbone polymer with a redox catalyst generally including a ceric or ferrous salt to generate one or more free radicals. The free radicals on the backbone polymer then react with the monomers that are present to literally grow in graft polymer from the backbone polymer.

Graft copolymers differ from IPN's in that a first polymer acts as a substrate onto which another polymer is added, or a site on the first polymer is involved in initiating polymerization to form a pendant polymer arm. Graft copolymers can readily be formed from polysaccharide or cellulosic backbones using methods well known in the art. Examples of such methods include the ceric salt redox method (U.S. Pat. No. 3,770,673 to Slagl et al.) and graft initiation using formaldehyde and sodium metabisulfite (U.S. Pat. No. 4,105,605 to Cottrell et al.). In order to achieve a high degree of grafting, heavy metal ions, such as cerium IV or ferrous, or reagents, such as formaldehyde, are used to augment the grafting reaction. In cases where a composition containing the graft copolymer is to be used on human skin and hair, the presence of heavy metal ions or formaldehyde is undesirable because they are considered by many to be cancer causing agents in humans, as well as environmentally harmful.

Further, graft copolymers are limited in the functional properties that they can provide. For example, the graft copolymer of U.S. Pat. No. 4,464,523 Neigel et al. has highly charged cationic arms and a neutral backbone. The possible polymer confirmations that allow such a polymer to interact with a keratin substrate are limited compared to a linear polymer. Further, the localized high charge density of the cationic arms can lead to incompatibility with many anionic surfactants, making it difficult to formulate with. These limitations result in inferior performance when such a polymer is used in keratin treating and/or cleansing compositions. For example, such polymers do not provide adequate wet combing properties when used in hair care formulations. Further the high localized charge density in cationic graft copolymers often leads to the polymer building up on the hair causing an undesirable property of the hair to not hold its shape especially after styling.

There remains a need for a polymeric conditioning additives for keratin based substrates that is easy to formulate with (easy to make clear surfactant based formulations), does not change over time, and provides excellent hair styling properties as well as excellent conditioning properties to hair, skin, and nails.

SUMMARY OF THE INVENTION

The present invention is directed to a composition for treating a keratin based substrate that includes a cosmetically acceptable medium containing a water-soluble polymer-polymer complex. The water-soluble polymer-polymer complex, or interjacent complex, includes a first water-soluble (a host polymer) polymer and a second water-soluble polymer formed by polymerizing one or more water-soluble monomers in the presence of the first water-soluble polymer (an intercalated polymer). The water-soluble interjacent complex is characterized in that it forms a solution in water that is free of insoluble polymer particles and maintains one uniform phase after standing at ambient conditions for at least three months.

The present invention is further directed to a method of treating a keratin based substrate. The method includes applying a cosmetically acceptable medium to the substrate. The cosmetically acceptable medium contains from 0.1–20% by weight of the present water-soluble interjacent complex.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "substantially free" is meant to indicate that a material can be present in an incidental amount or that a particular occurrence or reaction only takes place to an insignificant extent, which does not effect desired properties. In other words, the material is not intentionally added to an indicated composition, but may be present at minor or inconsequential levels, for example, because it was carried over as an impurity as part of an intended composition component.

As used herein, the terms "(meth)acrylic" and "(meth)acrylate" are meant to include both acrylic and methacrylic acid derivatives, such as the corresponding alkyl esters often referred to as acrylates and (meth)acrylates, which the term (meth)acrylate is meant to encompass.

As used herein, the term "active basis" refers to a concentration of additive based on the active solids in the stock solution.

As used herein, the term "polymer" is meant to encompass oligomer, and includes without limitation both homopolymers and copolymers.

As used herein, the phrase components "are different from each other" refers to components which do not have the same chemical structure as other components in the composition.

As used herein, the term "host polymer" refers to a polymer that is present during a polymerization reaction, but does not participate in initiating the polymerization reaction. The term "intercalated polymer" refers to the polymer that is formed in the presence of the host polymer.

As used herein, the terms "interjacent complex" and "polymer-polymer complex" refer to two polymers that are different from each other, and in intimate contact with each other. The interjacent or polymer-polymer complex is prepared by polymerizing monomers to form a polymer in the presence of a host polymer as described below. The interjacent complex is substantially free of grafting, which occurs only to the extent that chain transfer reactions to the host polymer occur.

As used herein, the term "water-soluble," when used in relation to polymers and interjacent complexes, refers to polymers and interjacent complexes that form a solution in water that is free of insoluble polymer particles. The determination that a solution is free of insoluble polymer particles can be made using conventional light scattering techniques or by passing the solution through a sufficiently fine filter screen capable of capturing insoluble polymer particles. As a non-limiting example, an aqueous solution containing 5 percent by weight of a polymer or interjacent complex can be prepared and poured through a U.S. Standard Sieve No. 100 (150 μm), and no particles are left on the screen. Alternatively, the turbidity of an aqueous solution containing 2.5 percent by weight of the polymer or interjacent complex, at a pH of from 5–9, may be measured using a turbidimeter or nephelometer. A reading of less than 20 nephelometric turbidity units (NTU) indicates the water-solubility of the polymer of interjacent complex.

As used herein, the terms "branching" and "branched polymers" refer to the arms of polymers that have a main backbone with arms extending therefrom, are not interconnected with other polymer molecules, and are water-soluble. Polymers that contain branching are distinguished from crossliked polymers in that crosslinked polymers are polymers that are branched and interconnected with other polymer molecules to the point that they form a three-dimensional network and are not water-soluble, while branched polymers retain their water solubility.

As used herein, the phrase "no visible phase separation" refers to the homogenous nature of the present interjacent complexes. "No visible phase separation" refers to solutions containing two or more polymers that maintain a single uniform phase after standing at ambient conditions for at least three months. In the present invention, the water-soluble interjacent complex, as prepared, does not separate into distinct phases after standing at ambient conditions for three months.

As used herein, the term "keratin" refers to human or animal hair, skin, and/or nails.

As used herein, the term "effective amount" refers to that amount of a composition necessary to bring about a desired result, such as, for example, the amount needed to treat a keratin-containing substrate relative to a particular purpose, such as conditioning.

As used herein the term "cosmetically acceptable medium" refers to formulations that are used to treat skin, hair, and/or nails and contain one or more ingredients used by those skilled in the art to formulate products used to treat skin, hair, and/or nails. The cosmetically acceptable medium may be in any suitable form, i.e., a liquid, cream, emulsion, gel, thickening lotion, or powder and will typically contain water and may contain a cosmetically acceptable solvent and/or one or more sufactants.

The present invention is directed to a composition for treating a keritin based substrate. The keratin treating composition includes a water-soluble interjacent complex made from:

(a) a water-soluble polymer; and (b) a polymer formed by polymerizing one or more water-soluble monomers in the presence of the polymer in (a) to form an intercalated polymer. The water-soluble interjacent complex may be characterized by its ability to form a solution in water that is free of insoluble polymer particles.

The present invention is further directed to a cosmetically acceptable medium containing an effective amount of the present interjacent complex. An effective amount in the cosmetically acceptable medium is at least 0.01 wt. %, in some cases, at least 0.1 wt. %, in other cases, at least 0.2 wt. %, in some instances, at least 0.25 wt. %, and in some situations, at least 0.5 wt. % of the cosmetically acceptable medium. Additionally, an effective amount of the interjacent complex in the cosmetically acceptable medium is up to 20 wt. %, in some cases, up to 15 wt. %, in other cases, up to 12.5 wt. %, in some instances, up to 10 wt. %, and in some situations, up to 5 wt. % of the cosmetically acceptable medium. The interjacent complex must be present at a level sufficient to provide its benefit but not a level where its use becomes cost prohibitive or interferes with the function of other components in the cosmetically acceptable medium.

The cosmetically acceptable medium may be an aftershave, a sunscreen, a hand lotion, a liquid soap, a bar soap, a bath oil bar, a shaving cream, a dishwashing liquid, a conditioner, a hair dye, a permanent wave, a hair relaxer, a hair bleach, a hair setting composition, a styling gel, or a shower gel. In a presently preferred embodiment, the interjacent complex concentration is from 0.1 to 10%, based on total medium weight.

The present invention is further directed to a method for treating a keratin-containing substrate comprising contacting the substrate with the above-defined interjacent complexes, typically, with an effective amount of the interjacent complexes or the cosmetically acceptable medium defined above containing an effective amount of the present interjacent complex. An effective amount of the interjacent complex in the present method is from 0.01 to 20 wt. %, in some cases, from 0.1 to 15 wt. %, in other cases, from 0.15 to 12.5 wt. %, and in some instances, from 0.20 to 10 wt. % based on the total weight of the medium.

The cosmetically acceptable medium will typically, also include surfactants and other commonly used components as outlined below.

The interjacent complex used herein is typically, a water-soluble interjacent complex prepared by polymerizing one or more water-soluble ethylenically unsaturated polymerizable monomers in the presence of a host polymer to form an intercalated polymer. The resulting water-soluble interjacent complex forms a solution in water that is free of insoluble polymer particles.

Any ethylenically unsaturated polymerizable monomer can be used in the present invention, so long as the resulting interjacent complex is water-soluble. Preferred monomers are those that promote water solubility or dispersibility. In this regard, preferred monomers include, but are not limited to, one or more of the following monomers; cationic monomers, such as acrylamidopropyltrimethyl ammonium chloride (APTAC), methacrylamidopropyltrimethyl ammonium chloride (MAPTAC), diallyl dimethyl ammonium chloride (DADMAC), acryloyloxyethyl trimethyl ammonium chloride (AETAC), and methacryloyloxyethyl trimethyl ammonium chloride (METAC); anionic monomers, such as 2-acrylamido-2-methylpropane sulfonic acid (AMPSA), 2-methacrylamido-2-methylpropane sulfonic acid (MAMPSA), sulfonated styrene, and vinyl sulfonic acid; allyl ether sulfonic acids, such as propane sulfonic acid allyl ether, methallyl ether phenyl sulfonates, (meth)acrylic acid, maleic acid, itaconic acid, n-(meth)acrylamidopropyl, n,n-dimethyl,amino acetic acid, n-(meth)acryloyloxyethyl, n,n-dimethyl,amino acetic acid, n-(meth)acryloyloxyethyl, n,n-dimethyl,amino acetic acid, crotonic acid, (meth)acrylamidoglycolic acid, and 2-(meth)acrylamido-2-methylbutanoic acid; and nonionic monomers, such as $C_1$–$C_{22}$ straight or branched chain alkyl or aryl (meth)acrylate, a $C_1$–$C_{22}$ straight or branched chain n-alkyl or aryl (meth)acrylamide, acrylamide, methylacrylamide, n-vinylpyrrolidone, vinyl acetate, ethoxylated, and propoxylated (meth)acrylate; hydroxy functional (meth)acrylates, such as hydroxyethyl(meth)acrylate and hydrocypropyl (meth)acrylate, n,n-dimethyl(meth)acrylamide; styrene and styrene derivatives; $C_1$–$C_{22}$ straight or branched chain alkyl, or aryl allyl ethers.

The interjacent complexes of the present invention are formed by polymerizing one or more of the above-described monomers in the presence of a host polymer. The host polymer can be a synthetic polymer, such as those produced by free radical polymerization or condensation polymerization or it may be a natural polymer, such as a natural gum, a starch, a modified starch, a cellulosic, a modified cellulosic, a water-soluble natural gum, water-soluble modified natural gums, proteins, or protein derivatives. Examples of host polymers that can be used in the present invention include, but are not limited to, vinyl polymers, water-soluble olefin containing copolymers, water-soluble polyacrylates, water-soluble polyamides, water-soluble polyesters, water-soluble polyurethanes, xanthan gums, sodium alginates, galactomanans, carageenan, gum arabic, cellulose and its derivatives, such as hydroxyethyl cellulose and hydroxypropyl cellulose, starch and its derivatives, guar and its derivatives, proteins and their derivatives, water-soluble poly(meth)acrylates, water-soluble polyamides, water-soluble polyesters, water-soluble polyurethanes, water-soluble poly(vinyl alcohol), water-soluble poly (vinyl amine), water-soluble poly(ethylene imine), water-soluble amine/epihalohydrin polyamines, water-soluble poly(meth)acrylamide, water-soluble (meth)acrylamide copolymers, water-soluble poly(meth)acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth)acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, and copolymers of (meth)acryloyloxyethyltrimethyl ammonium methyl sulfate.

The molecular weight (Mw) of the host polymer and the intercalated polymer will both be at least 1,000, in some cases, at least 5,000, in other cases, at least 10,000, in some instances, at least 20,000 and in other instances at least 25,000 or 50,000. On occasion, the molecular weight of the host polymer and the intercalated polymer will both be not more than 10,000,000, in some cases, not more than 5,000,000, in other cases, not more than 2,500,000, in some instances, not more than 1,000,000 and in other instances not more than 500,000. The actual molecular weight of the host polymer and the intercalated polymer is determined based on the intended use and properties desired in the interjacent complex. The molecular weight of the host polymer and the intercalated polymer may be any value or any range of values inclusive of those stated above. The molecular weight (Mw) of the host polymer and the intercalated polymer may be determined by viscometry in a Ubbelhhde Capillary Viscometer at 0.05% by weight concentration of the host polymer or intercalated polymer in 1M NaCl solution, at 30° C., pH 7. The reduced viscosity measured under such conditions may range from 0.1 to 20 dl/g, in some cases, 0.25 to 15 dl/g, in other cases, 0.5 to 12.5 dl/g, and in other instances, 1 to 10 dl/g. Alternatively, gel permeation chromatography (GPC) using appropriate standards can be used to determine molecular weight, in which case the Mw value is used as the molecular weight measurement.

A class of polymers that are particularly useful in the present invention as host polymers include those referred to as polyquaterniums. Preferred polyquaterniums include those described in the *International Cosmetic Ingredient Dictionary*, published by the Cosmetic, Toiletry, and Fragrance Association (CTFA), 1101 17$^{th}$ Street, N.W., Suite 300, Washington, D.C. 20036. Examples of such polyquaterniums include, but are not limited to (1) the polymeric quaternary ammonium salt of hydroxyethyl cellulose reacted with a trimethyl ammonium substituted epoxide, referred to as Polyquaternium-10; (2) the quaternary ammonium derivative of hydroxypropyl guar, referred to as guar hydroxypropyltrimonium chloride; (3) the copolymer of hydroxyethylcellulose and DADMAC, referred to as Polyquaternium-4; (4) the copolymer of acrylamide and METAMS, referred to as Polyquaternium-5; (5) the homopolymer of DADMAC, referred to as Polyquaternium-6; (6) The copolymer of acrylamide and DADMAC, referred to as Polyquaternium-7; (7) the copolymer of vinyl pyrrolidone and METAMS, referred to as Polyquaternium-11; (8) the homopolymer of METAMS, referred to as Polyquaternium-14; (9) the copolymer of methacrylamide and METAMS, referred to as Polyquaternium-15; (10) the polymeric quaternary ammonium salt of hydroxyethyl cellulose reacted with a lauryl dimethyl ammonium substituted epoxide, referred to as Polyquaternium-24; (11) the copolymer of vinyl pyrrolidone and MAPTAC, referred to as Polyquaternium-28; (12) the copolymer of acrylamide and METAC, referred to as Polyquaternium-32; (13) the copolymer of acrylamide and AETAC, referred to as Polyquaternium-33; (14) the copolymer of butylmethacrylate, dimethylaminoethylmethacrylate, and METAMS, referred to as Polyquatemium-36; (15) the homopolymer of METAC, referred to as Polyquaternium-37; (16) the copolymer of METAMS, methyl methacrylate, and hydroxyethylmethacrylate, referred to as Polyquaternium-45; (17) the homopolymer of MAPTAC, referred to as polymethacrylamidopropyltrimonium chloride; (18) Hydroxypropyl trimethyl ammonium chloride ether derivatives of starch, as generally described by the CAS Registry Number 5670-58-6, the starch of which can be derived from a variety of natural sources such as corn, potato, rice, tapioca, wheat, or other sources; (19) the copolymer of DADMAC and acrylic acid, referred to as Polyquaternium-22; (20) the copolymer of DADMAC, acrylic acid, and acrylamide, referred to as Polyquaternium-39; and (21) the copolymer of MAPTAC, acrylic acid, and methyl(meth)acrylate, referred to at Polyquaternium-47.

One or more host polymers may be used to prepare the present water-soluble interjacent complex. The host polymer is present during the polymerization and formation of the intercalated polymer. As such it is present at a level of at least 0.01 wt. %, in some cases, at least 0.1 wt. %, in other cases, at least 0.5 wt. %, in some instances, at least 1.0 wt. % and in other instances, at least 5 wt. % based on the total weight of monomer and host polymer in the composition of the interjacent complex. The host polymer is present at a level that will allow its beneficial properties to be ascertainable. The level of the host polymer in the interjacent complex can be up to 95 wt. %, in some cases, up to 75 wt. %, in other cases, up to 50 wt. %, in some instances, up to 25 wt. % and in other instances up to 10 wt. % based on the total weight of monomer and host polymer in the composition of the interjacent complex. The maximum limit for the host polymer is determined by the properties desired in the interjacent complex and the molecular weight of the host polymer. The host polymer level is not so high as to make the polymerization medium too highly viscous as to deter thorough mixing of the host polymers and monomers for the intercalated polymer. The amount of host polymer in the present interjacent complex can be any level or range of the levels recited above.

In an embodiment of the present invention, the interjacent complex includes an intercalated polymer prepared in the presence of one or more of the above-mentioned host polymers. The polymerization is carried out using a monomer composition including: (a) 0 to 100 mol %, typically, 5 to 90 mol %, in some cases, 10 to 75 mol % and in other cases, 20 to 50 mol % of a cationic monomer; (b) 0 to 100 mol %, typically, 5 to 50 mol %, in some cases, 10–50 mol % and in other cases, 20 to 45 mol % of an anionic monomer; (c) 0 to 100 mol %, typically, 10 to 90 mol %, in some cases, 15–75 mol % and in other cases, 20 to 60 mol % of a nonionic monomer polymerized in the presence of the host polymer. In this embodiment (a), (b) and (c) are different from each other and the total mol % for (a), (b), and (c) is 100 mol %.

In a further embodiment, the present invention is directed to a water-soluble interjacent complex prepared by polymerizing a monomer mixture that includes (a) a cationic monomer; (b) a sulfonic acid containing anionic monomer; (c) a carboxylic acid containing anionic monomer; and (d) a nonionic monomer in the presence of one or more of the above-mentioned host polymers.

When included, the cationic monomer is present in the intercalated polymer at a level of at least 5 mol %, in some cases, at least 10 mol %, in other cases, at least 15 mol %, and in some instances, at least 20 mol % based on the total monomer composition of the intercalated polymer. When used, the cationic monomer must be present at a level that will promote surface interaction and substantivity of the present interjacent complex to the keratin substrate. When used, the level of cationic monomer in the intercalated polymer can be up to 95 mol %, in some cases, up to 85 mol %, in other cases, up to 75 mol %, and in some instances, up to 60 mol % based on the total monomer composition of the intercalated polymer. When the level of cationic monomer is too high, the present interjacent complex may become difficult to formulate in compositions containing anionic surfactants. The amount of cationic monomer in the present intercalated polymer can be any level or range of the levels recited above.

When included, the sulfonic acid functional anionic monomer is included in the present intercalated polymer at a level of at least 1 mol %, in some cases, at least 5 mol %, in other cases, at least 7.5 mol %, and in some instances, at least 10 mol %. The sulfonic acid functional anionic monomer is present at a level sufficient to promote compatibility with anionic surfactant containing formulations. When included, the level of sulfonic acid functional anionic monomer is present in the intercalated polymer at up to 80 mol %, in some cases, to 70 mol %, in other cases, up to 60 mol %, and in some instances, up to 50 mol % based on the total monomer composition of the intercalated polymer. If the level of sulfonic acid functional anionic monomer is too high, the present interjacent complex becomes difficult to formulate in cosmetically acceptable compositions and substantivity may be diminished. The amount of sulfonic acid functional anionic in the intercalated polymer of the present invention may be any level or range of the levels recited above.

The carboxylic acid functional anionic monomer is optionally included in the intercalated polymer. When the carboxylic acid functional anionic monomer is included, it is included at a level of at least 1 mol %, in some cases, at least 5 mol %, in other cases, at least 10 mol %, and in some instances, at least 15 mol %. The carboxylic acid functional anionic monomer is present at a level sufficient to promote compatibility with anionic surfactant containing formulations. The level of carboxylic acid functional anionic monomer in the intercalated polymer can be up to 80 mol %, in some cases, up to 50 mol %, in other cases, up to 40 mol %, in some instances, up to 30 mol %, and in other instances up to 25 mol % based on the overall intercalated polymer composition. If the level of carboxylic acid functional anionic monomer is too high, the present interjacent complex becomes difficult to formulate in cosmetically acceptable compositions and substantivity may be diminished. The amount of carboxylic acid functional anionic monomer in the present intercalated polymer can be any level or range of levels recited above.

The nonionic monomer is optionally included in the intercalated polymer. When the nonionic monomer is included, it is included at a level of at least 5 mol %, in some cases, at least 10 mol %, in other cases, at least 15 mol %, and in some instances, at least 20 mol %. The nonionic monomer promotes hydrogen bonding between the present interjacent complex and the keratin substrate and also promotes desirable film-forming properties of the present interjacent complex. The level of nonionic monomer in the intercalated polymer can be up to 99 mol %, in some cases, 90 mol %, in other cases, up to 60 mol %, in some instances, up to 50 mol %, and in other instances up to 45 mol % based on the overall intercalated polymer composition. If the level of nonionic monomer is too high, substantivity may be poor. The amount of nonionic monomer in the intercalated polymer can be any level or range of levels recited above.

In an embodiment of the present invention, when one or more nonionic monomers are included in the intercalated polymer, the intercalated polymer may include from 20 to 95 mol %, in some cases, 20 to 50 mol %, in other cases, 25 to 50 and in some instances, 30 to 45 mol % of a cationic monomer; (b) 0 to 80 mol %, in some cases, 5 to 40 mol %, in other cases, 5–30 mol %, and in some instances, 5 to 25 mol % of a sulfonic acid functional anionic monomer; (c) 0–55 mol %, in some cases, 5 to 50 mol %, in other cases, 10 to 45 mol %, and in some instances, 15 to 45 mol % of nonionic monomer; and (d) 0–25 mol %, in some cases, 5 to 25 mol %, in other cases, 10–25 mol %, and in some instances, 15–25 mol % carboxylic acid functional anionic monomer. The sum of the total amount of monomers in (a), (b), (c), and (d) is always 100 mol %.

Any suitable cationic monomer may be used to make the intercalated polymer of the present invention. Presently preferred cationic monomers include, but are not limited to, acrylamidopropyltrimethyl ammonium halide (APTAH), methacrylamidopropyltrimethyl ammonium halide (MAPTAH), diallyl dimethyl ammonium halide (DADMAH), acryloyloxyethyl trimethyl ammonium halide (AETAH), and methacryloyloxyethyl trimethyl ammonium halide (METAH). In an embodiment of the present invention, the halides are selected from chloride, bromide, and iodide.

Any suitable sulfonic acid containing anionic monomer may be used to make the intercalated polymer of the present invention. Presently preferred sulfonic acid containing anionic monomers include, but are not limited to, 2-acrylamido-2-methylpropane sulfonic acid (AMPSA), 2-methacrylamido-2-methylpropane sulfonic acid (MAMPSA), sulfonated styrene, vinyl sulfonic acid, allyl ether sulfonic acids, such as propane sulfonic acid, allyl ether, and methallyl ether phenyl sulfonates.

In an embodiment of the present invention, the mol ratio of cationic monomer to sulfonic acid containing anionic monomer in the intercalated polymer ranges from 20:80 to 95:5, typically, from 25:75 to 75:25.

Any suitable nonionic monomer may be used to make the intercalated polymer of the present invention. Presently preferred nonionic monomers include, but are not limited to, $C_1$–$C_{22}$ straight or branched chain alkyl or aryl (meth) acrylate, a $C_1$–$C_{22}$ straight or branched chain n-alkyl or aryl (meth)acrylamide, acrylamide, methylacrylamide, n-vinylpyrrolidone, vinyl acetate, ethoxylated, and propoxylated (meth)acrylate, hydroxy functional (meth)acrylates, such as hydroxyethyl(meth)acrylate and hydrocypropyl (meth)acrylate, n,n-dimethyl(meth)acrylamide, styrene and styrene derivatives, $C_1$–$C_{22}$ straight or branched chain alkyl, or aryl allyl ethers.

Any suitable carboxylic acid containing anionic monomer may be used to make the intercalated polymer of the present invention. Presently preferred carboxylic acid containing monomers include, but are not limited to, (meth)acrylic acid, maleic acid, itaconic acid, N-(meth)acrylamidopropyl,N,N-dimethyl,amino acetic acid, N-(meth)acryloyloxyethyl,N,N-dimethyl,amino acetic acid, N-(meth)acryloyloxyethyl,N,N-dimethyl,amino acetic acid, crotonic acid, (meth) acrylamidoglycolic acid, and 2-(meth)acrylamido-2-methylbutanoic acid.

As was described above, the present interjacent complex includes a host polymer and an intercalated polymer. The weight ratio of the two polymers in the interjacent complex will vary depending on the properties desired from the interjacent complex. When an excess of host polymer is desired, the weight ratio of the host polymer to the inercalated polymer may be 100:1, in some cases, 75:1, in other cases, 50:1, in some instances, 25:1, in other instances, 10:1, and often times, 5:1. In an embodiment of the present invention, the weight ratio of the host polymer to the intercalated polymer is 1:1. When it is desirable to have the intercalated polymer present in excess, the weight ratio of the host polymer to the intercalated polymer may be 1:100, in some cases, 1:75, in other cases, 1:50, in some instances, 1:25, in other instances, 1:10, and often times, 1:5. The weight ratio of the host polymer to the intercalated polymer in the interjacent polymer complex may range between any of the ratios recited above.

The interjacent complexes of the present invention provide several advantages when compared to physical blends of comparable polymers. The interjacent complexes provide a means of formulating with highly charged polymers in formulations that would otherwise be incompatible with such ingredients in the formulation. Solutions of the present interjacent complex demonstrate improved stability, i.e., less or no visible phase separation over time, than comparable physical blends or mixtures of comparable polymers. The interjacent complexes provide a means of delivering a highly charged polymer to the surface of dispersed solids in an aqueous system. Further, the combined action of the two polymers, as complexed herein, provide enhanced and synergistic performance and physical properties compared to physical blends or mixtures of comparable polymers.

The weight average molecular weight of the interjacent complex, as determined by viscometry, is at least 1,000, typically, from 10,000 to 10,000,000, more typically, from 25,000 to 8,000,000, and most typically, from 50,000 to 5,000,000. Alternatively, gel permeation chromatography (GPC) using appropriate standards can be used to determine molecular weight, in which case the Mw value is used as the molecular weight measurement. The molecular weight (Mw) of the interjacent complex may be determined by viscometry in a Ubbelhhde Capillary Viscometer at 0.05% by weight concentration of the interjacent complex in 1M NaCl solution, at 30° C., pH 7. The reduced viscosity measured under such conditions may range from 0.1 to 20 dl/g, in some cases, 0.25 to 15 dl/g, in other cases, 0.5 to 12.5 dl/g, and in other instances, 1 to 10 dl/g. Alternatively, gel permeation chromatography (GPC) using appropriate standards can be used to determine molecular weight, in which case the Mw value is used as the molecular weight measurement.

The present interjacent complexes may be prepared by conventional solution polymerization techniques or alternatively by water-in-oil emulsion polymerization techniques. When prepared as a solution polymerization, the polymer and monomer(s) are combined in an aqueous solution and the monomers are polymerized.

In an oil-in-water emulsion system, the host polymer and monomer(s) are combined in an aqueous solution and dispersed in a suitable hydrocarbon continuous phase to form discrete droplets dispersed within the hydrocarbon. A suitable initiator is then added to the water-in-oil emulsion, which is allowed to polymerize in either an adiabatic or isothermal mode. In an alternative embodiment, an oil soluble monomer can be added after the above-described polymerization step, and subsequently polymerized using a suitable initiator to form core-shell dispersed particles. In this alternative embodiment, the outer surface, or shell, of the particle contains the polymerized oil soluble monomer, and the inner portion, or core, contains the interjacent complex.

In an embodiment of the present invention, the interjacent complex is formed via a solution polymerization. To prepare the present interjacent complex, the appropriate weights for the desired mol percentages of monomers, for example, cationic monomer, sulfonic acid containing anionic monomer, carboxylic acid containing anionic monomer and nonionic monomer, together with one or more of the above-mentioned host polymers are charged to a glass reactor equipped with a stirring means. The desired total monomer concentration is generally about 10–30% by weight. The monomer mixture may then be adjusted to a pH of about 2.0 to about 6.5 with dilute NaOH, heated to about 55° C., and purged with nitrogen for at least thirty minutes. Polymerization is then initiated by adding $5 \times 10^{-2}$ mol % of sodium persulfate and $2.4 \times 10^{-3}$ mol % of sodium bisulfate. After the peak exotherm is reached, additional dilution water and sodium bisulfite are added to scavenge any residual monomer and to dilute the final product polymer solids. The use of ceric or ferrous ions is avoided so as to not promote grafting cations. In other words, the present polymerization is conducted in the substantial absence of ceric, ferrous, or ferrous ions.

Regardless of the preparation process employed, the host polymer and the intercalated polymer can be polymers made using different manufacture techniques. For example one polymer can be made using an adiabatic process, which will typically, result in a wide molecular weight and polymer composition distribution. The other polymer can be prepared using an isothermal process, which will typically, provide a polymer with a narrow molecular weight distribution. The resulting interjacent complex resulting from the combination of the two manufacturing processes results in unique properties for the resulting complex.

The intercalated polymer derived from polymerizing the above mentioned monomers in the presence of a host polymer may be branched by including suitable "crosslinking" monomers in the polymerization process. A crosslinking monomer is one or more monomers that have two or more sites of reactive unsaturation. Typically, a branching quantity of one or more monomers that have two or more sites of reactive unsaturation are used in addition to the above-described monomers to make the intercalated polymer. The branching quantity of the monomers having two or more sites of reactive unsaturation may be from 0.0001 to 0.1 mol %, in some cases, 0.001 to 0.09 mol %, in other cases, 0.01 to 0.075 mol % in some instances, 0.015 to 0.05 mol %, and in other instances 0.02 to 0.03 mol % based on the total number of mols of monomers used to make the intercalated polymer.

Examples of monomers having two or more sites of reactive unsaturation that may be used in the present invention include, but are not limited to, ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth)acrylate, pentaerythritol di(meth)acrylate, pentaerythritol tri(meth)acrylate, pentaerythritol tetra(meth)acrylate, glycerol di(meth)acrylate, glycerol allyloxy di(meth)acrylate, 1,1,1-tris(hydroxymethyl)ethane di(meth)acrylate, 1,1,1-tris(hydroxymethyl)ethane tri(meth)acrylate, 1,1,1-tris(hydroxymethyl)propane di(meth)acrylate, 1,1,1-tris(hydroxymethyl)propane tri(meth)acrylate, triallyl cyanurate, triallyl isocyanurate, triallyl trimellitate, diallyl phthalate, diallyl terephthalte, divinyl benzene, triallylamine, and methylenebis (meth) acrylamide.

Further, the interjacent complexes of the present invention may be purified, or provided in "narrow" molecular weight form, through art recognized methods of polymer fractionation by using poor solvents and/or non-solvents for the interjacent complex. Other methods of fractionating the interjacent complex include, but are not limited to, precipitation and membrane separation, including the use of cross-flow membranes.

Reduced viscosity (dl/g) may be used as an approximate measure of the weight average molecular weight of the interjacent complexes of the present invention. The values may be determined using a Ubbelhhde Capillary Viscometer at 0.05% concentration of polymer in a 1M NaCl solution, pH 7, at 30° C. The resulting molecular weight value is calculated in accordance with methods well known in the art. The reduced viscosity of the interjacent complex of the present invention is from 0.1 to 20 dl/g, in many cases, 0.5 to 15 dl/g, typically, 0.75 to 12.5 dl/g, and in some cases, 1 to 10 dl/g.

Not wishing to be bound to any single theory, it is believed that during the polymerization process, a minimal amount of grafting onto the host polymer may take place due to chain transfer to polymer reactions. However, the great bulk and majority of the host polymer molecules and intercalated polymer molecules are not grafted, interlinked or in any way covalently bonded to each other. Further, it is believed that the host polymer and the intercalated polymer form a structure where hydrophobic domains in the polymer molecules may associate with each other, oppositely charged ionic or dipolar species in each polymer may associate with each other as well as other forces, such as Van der Walls and hydrogen bonding, act to maintain the polymer molecules in intimate association with each other. These associations may mimic many commonly observed properties observed in IPNs. The interjacent complex that is formed in the present invention cannot be formed through physical mixing and does not phase separation on standing, dissociate on dilution, or physical manipulation of the interjacent complex. These polymer-polymer interactions and entanglements aid in stabilizing the interjacent complex that forms and minimizes the potential negative consequences that may occur due to, for example, poly salt formation. Laboratory experiments indicate that the two polymer components in the present interjacent complex cannot be separated by conventional separation techniques, indicating the unique structure that is formed between the two polymers.

The interjacent complexes of the present invention provide several advantages in personal care applications. The interjacent complexes provide a means of formulating with highly charged polymers in formulations that would otherwise be incompatible with the ingredients of the formulation. The interjacent complexes provide a means of delivering the highly charged polymer to the keratin substrate. Further, the combined action of the two polymers, as complexed herein, provide enhanced and synergistic conditioning properties to hair, skin, and nails not available in prior art formulations.

The interjacent complexes may be added to a cosmetically acceptable medium at a concentration of from 0.1 to 10% by weight based on total medium weight. Methods of adding the instant interjacent complexes to a cosmetically acceptable medium are well known to those familiar with the art. The best mode also entails use of an effective amount of the interjacent complex containing medium in the treatment of a keratin-containing substrate, typically, human skin or hair. Methods of using such compositions are well known in the art.

The interjacent complexes of the present invention are used in compositions for treating hair, skin, or nails by incorporating them in a cosmetically acceptable medium used to treat hair, skin, or nails in amounts of about 0.01 to about 20% on an active polymer basis based on the total weight of said medium and typically in an amount of from about 0.1 to about 10% active polymer based on total medium weight.

These compositions can be presented in various forms, i.e., various cosmetically acceptable media, such as a liquid, cream, emulsion, gel, thickening lotion, or powder; they can contain water and also any cosmetically acceptable solvent, in particular, monoalcohols, such as alkanols having 1 to 8 carbon atoms (like ethanol, isopropanol, benzyl alcohol and phenylethyl alcohol), polyalcohols, such as alkylene glycols (like glycerine, ethylene glycol and propylene glycol), and glycol ethers, such as mono-, di-, and tri-ethylene glycol monoalkyl ethers, for example, ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol; in which case, they can be applied either in the form of an aerosol spray or in the form of an aerosol foam. As the propellant gas for these aerosols, it is possible to use, in particular, dimethyl ether, carbon dioxide, nitrogen, nitrous oxide, and volatile hydrocarbons, such as butane, isobutane, propane, and possibly, chlorinated and fluorinated hydrocarbons, although the latter are falling into increasing environmental disfavor.

Preferred compositions can also contain electrolytes, such as aluminum chlohydrate, alkali metal salts, e.g., sodium, potassium, or lithium salts, these salts typically, being halides, such as the chloride or bromide, and the sulfate, or salts with organic acids, such as the acetates or lactates, and also alkaline earth metal salts, typically, the carbonates, silicates, nitrates, acetates, gluconates, pantothenates and lactates of calcium, magnesium and strontium. Any of these active ingredients can alternatively be incorporated with the interjacent complex of the present invention by including them in the polymerization step described above. Further, these active ingredients may be used in place of the host polymer.

These compositions can also be presented in the form of a powder or of lyophilisates to be diluted before use.

The compositions according to the present invention can contain any other ingredient normally used in cosmetics, such as perfumes, dyestuffs, which can serve to color the composition itself, or hair fibers, preservatives, sequestering agents, thickeners, silicones, softeners, foam synergistic agents, foam stabilizers, sun filters, peptising agents, and also anionic, non-ionic, cationic, or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming, or before or after straightening, and can also adopt the form of a coloring product, a setting lotion, a brushing lotion, a bleaching product, a perming product, or a straightening product.

A particularly preferred embodiment consists of use in the form of a shampoo for washing the hair.

In this case, these compositions contain anionic, nonionic, or amphoteric surface-active agents typically, in an amount from 3–50% by weight, typically, 3–20%, and their pH is generally in the range of 3 to 10.

The keratin cleansing compositions of the present invention typically, contain an anionic surfactant, which can comprise one or more anionic detersive surfactants, which are anionic at the pH of the composition, to provide cleaning performance to the composition.

The anionic surfactant can be the only surfactant and will generally be present at a level from about 2% to about 50%, typically, from about 5% to about 30%, more typically, from about 6% to about 25%, of the composition, with about 10% to about 15% being most preferred. For cleansing compositions, the anionic surfactant is the preferred surfactant and is typically, present in the composition in combination with a second surfactant that is not cationic.

Anionic detersive surfactants useful herein include those that are disclosed in U.S. Pat. No. 5,573,709 to Wells, the disclosure of which is herein incorporated by reference in its entirety. Examples include alkyl and alkyl ether sulfates. Specific examples of alkyl ether sulfates which may be used in the present invention are sodium and ammonium salts of lauryl sulfate, lauryl ether sulfate, coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic detersive surfactants are the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, typically, about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfated $C_{12}$–$C_{38}$ n-paraffins.

Additional examples of synthetic anionic detersive surfactants which come within the terms of the present invention are the olefin sulfonates, the beta-alkyloxy alkalene sulfonates, and the reaction products of fatty acids esterified with isethionic acid and neutralized with sodium hydroxide, as well as succinamates. Specific examples of succinamates include disodium N-octadecyl sulfofosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Many additional synthetic anionic surfactants are described in U.S. Pat. No. 3,929,678 to Laughlin et al., which is herein incorporated by reference in its entirety.

Preferred anionic detersive surfactants for use in the present compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine 1 lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

The keratin cleansing compositions of the present invention typically, contain an amphoteric detersive surfactant. The amount of this surfactant is typically, no more than about 10 weight %. Examples of amphoteric detersive surfactants which can be used in the compositions of the present invention are those which are broadly described as derivatives of aliphatic secondary and tertiary amines in which the aliphatic substituent contains from about 8 to 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines, such as the one prepared by reacting dodecylamine with sodium isethionate according to the teaching of U.S. Pat. No. 2,658,072 to Kosmin, N-higher alkyl aspartic acids, such as those produced according to the teaching of U.S. Pat. No. 2,438,091 to Lynch, and the products described in U.S. Pat. No. 2,528,378 to Mannheimer.

In addition to the anionic detersive surfactant component, the keratin cleansing compositions of the present invention can optionally contain other detersive surfactants. These include nonionic surfactants, cationic surfactants, and zwitterionic surfactants. Optional detersive surfactants, when used, are typically, present at levels of from about 0.5% to about 20%, more typically, from about 1% to about 10%, although higher or lower levels can be used. The total amount of detersive surfactant in compositions containing optional detersive surfactants in addition to the anionic surfactant will generally be from about 5% to about 40%, typically, from about 8% to about 30%, more typically, from about 10% to about 25%.

Nonionic detersive surfactants which can be used include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; the alkyl polysaccharide (APS) surfactants, such as the alkyl polyglycosides; and the polyethylene glycol (PEG) glyceryl fatty esters.

Zwitterionic surfactants, such as betaines, can also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine, and the like; amidobetaines; and amidosulfobetaines, wherein the $RCONH(CH_2)_3$ radical is attached to the nitrogen atom of the betaine, are also useful in this invention.

Preferred compositions of the present invention are shampoos, shower gels, and liquid hand soaps, and these typically, contain combinations of anionic surfactants with zwitterionic surfactants and/or amphoteric surfactants. Especially preferred keratin cleansing compositions contain from about 0% to about 16% of alkyl sulfates, from 0% to about 16% of ethoxylated alkyl sulfates, and from about 0% to about 10% of optional detersive surfactants selected from the nonionic, amphoteric, and zwitterionic detersive surfactants, with at least 5% of either alkyl sulfate, ethoxylated alkyl sulfate, or a mixture thereof, and a total surfactant level of from about 10% to about 25%.

The keratin treating compositions of the present invention optionally contain a nonvolatile, water insoluble, organic, oily liquid as a preferred type of conditioning agent. The conditioning oily liquid can protect, lubricate, and/or moisturize the skin and add shine, softness, and luster to the hair. Additionally, it can also enhance dry combing and dry hair feel. The hair conditioning oily liquid is typically, present in the compositions at a level of from about 0.05% to about 5%, by weight of the composition, typically, from about 0.2% to about 3%, more typically, from about 0.5% to about 1%.

For skin care formulations, oil in water emulsions will contain amounts, by weight, of the organic insoluble liquid of about 3 to about 25%, typically, about 5 to about 20%, with about 6 to 15% being most preferred. Water-in-oil skin care formulations will contain amounts, by weight, of the organic insoluble liquid of about 25 to about 70%, typically, about 30 to about 60%, with about 35 to about 50% being most preferred.

By "nonvolatile" what is meant is that the oily material exhibits very low or no significant vapor pressure at ambient conditions (e.g., 1 atmosphere, 25° C.), as is understood in the art. The nonvolatile oily materials typically, have a boiling point at ambient pressure of about 250° C. or higher.

By "water insoluble" what is meant is that the oily liquid is not soluble in water (distilled or equivalent) at a concentration of 0.1%, at 25° C.

The conditioning oily liquids hereof generally will have a viscosity of about 3 million cs or less, typically, about 2 million cs or less, more typically, about 1.5 million cs or less.

The conditioning oily materials hereof are liquids selected from the group consisting of hydrocarbon oils and fatty esters. The fatty esters hereof are characterized by having at least 12 carbon atoms, and include esters with hydrocarbon chains derived from fatty acids or alcohols, e.g., monoesters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages, etc.).

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will typically contain from about 12 to about 19 carbon atoms, although it is not necessarily meant to limit the hydrocarbons to this range. Branched chain hydrocarbon oils can and typically, may contain higher numbers of carbon atoms. Also encompassed herein are polymeric hydrocarbons of alkenyl monomers, such as $C_2$–$C_6$ alkenyl monomers. These polymers can be straight or branched chain polymers. The straight chain polymers will typically, be relatively short in length, having a total number of carbon atoms as described above for straight chain hydrocarbons in general. The branched chain polymers can have substantially higher chain length. The number average molecular weight of such materials can vary widely but will typically, be up to about 500, typically, from about 200 to about 400, more typically, from about 300 to about 350.

Specific examples of suitable materials include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and undecane, such as 2, 2, 4, 4, 6, 6, 8, 8-dimethyl-10-methylundecane and 2, 2, 4, 4, 6, 6-dimethyl-8-methyinonane, sold by Permethyl Corporation. A preferred hydrocarbon polymer is polybutene, such as the copolymer of isobutylene and butene. A commercially available material of this type is L-19 polybutene from Amoco Chemical Co. (Chicago, Ill., USA)

Monocarboxylic acid esters hereof include esters of alcohols and/or acids of the formula R' COOR wherein alkyl or alkenyl radicals and the sum of carbon atoms in R' and R is at least 10, typically, at least 20.

Fatty esters include, for example, alkyl and alkenyl esters of fatty acids having aliphatic chains with from about 10 to about 22 carbon atoms, and alkyl and alkenyl fatty alcohol carboxylic acid esters having an alkyl and/or alkenyl alcohol-derived aliphatic chain with about 10 to about 22 carbon atoms, and combinations thereof. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyl decyl adipate, lauryl lactate, myristyl lactate, cetyl lactate, oleyl stearate, oleyl oleate, oleyl myristate, lauryl acetate, cetyl propionate, and oleyl adipate.

The mono-carboxylic acid ester however needs not necessarily contain at least one chain with at least 10 carbon atoms, so long as the total number of aliphatic chain carbon atoms is at least 10. Examples include diisopropyl adipate, diisohexyl adipate, and diisopropyl sebacate.

Di- and tri-alkyl and alkenyl esters of carboxylic acids can also be used. These include, for example, esters of $C_4$–$C_8$ dicarboxylic acids, such as $C_1$–$C_{22}$ esters (typically, $C_1$–$C_6$) of succinic acid, glutaric acid, adipic acid, hexanoic acid, heptanoic acid, and octanoic acid. Specific examples include isocetyl stearyl stearate, diisopropyl adipate, and tristearyl citrate. Polyhydric alcohol esters include alkylene glycol esters, for and di-fatty acid esters, diethylene example ethylene glycol mono glycol mono- and di-fatty acid esters, polyethylene glycol mono and di-fatty acid esters, propylene glycol mono-, and di-fatty acid esters, polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory polyhydric alcohol esters for use herein.

Glycerides include mono-, di-, and tri-glycerides. More specifically, included are the mono-, di-, and tri-esters of glycerol and long chain carboxylic acids, such as $C_{10}$–$C_{22}$ carboxylic acids. A variety of these types of materials can be obtained from vegetable and animal fats and oils, such as castor oil, safflower oil, cotton seed oil, corn oil, olive oil, cod liver oil, almond oil, avocado oil, palm oil, sesame oil, lanolin, and soybean Synthetic oils include triolein and tristearin glyceryl dilaurate. Preferred glycerides are di- and tri-glycerides. Especially preferred are triglycerides.

The keratin treating compositions of the present invention optionally contain a nonvolatile, nonionic silicone conditioning agent which is insoluble in the compositions hereof. The silicone conditioning agent is intermixed in the composition so as to be in the form of dispersed, insoluble particles, or droplets. The silicone conditioning agent comprises a nonvolatile, insoluble, silicone fluid and optionally comprises a silicone gum which is insoluble in the composition as a whole but is soluble in the silicone fluid. The silicone conditioning agent can also comprise other ingredients, such as a silicone resin, to enhance deposition efficiency.

The silicone conditioning agent may comprise low levels of volatile silicone components; however, such volatile silicones will typically, exceed no more than about 0.5%, by weight, of the composition. Typically, if volatile silicones are present, it will be incidental to their use as a solvent or carrier for commercially available forms of other ingredients, such as silicone gums and resins The silicone conditioning agent for use herein will typically, have a viscosity of from about 1,000 to about 2,000,000 centistokes at 25° C., more typically, from about 10,000 to about 1,800,000, even more typically, from about 100,000 to about 1,500,000. The viscosity can be measured by means of a glass capillary viscometer as set forth in Dow Corning Corporate Test Method CTM0004, Jul. 20, 1970.

The silicone conditioning agent will be used in the compositions hereof at levels of from about 0.5% to about 10% by weight of the composition, typically, from about 0.1% to about 10%, more typically, from about 0.5% to about 8%, most typically, from about 0.5% to about 5%. The silicone conditioning agent is also typically, used in combination with the organic water insoluble liquid.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having conditioning properties can also be used. The term "nonvolatile" as used herein shall mean that the silicone material exhibits very low or no significant vapor pressure at ambient conditions, as is understood by those in the art. The term "silicone fluid" shall mean flowable silicone materials having a viscosity of less than 1,000,000 centistokes at 25° C. Generally, the viscosity of the fluid will be between about 5 and 1,000,000 centistokes at 25° C., typically, between about 10 and about 100,000.

The nonvolatile polyalkylsiloxane fluids that may be used include, for example, polydimethyl siloxanes. These siloxanes are available, for example, from the General Electric Company in their Viscasil® and SF 96 series and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

References disclosing suitable silicone fluids include U.S. Pat. No. 2,826,551 to Geen; U.S. Pat. No. 3,964,500 to Drakoff; U.S. Pat. No. 4,364,837 to Pader; U.S. Pat. No. 5,573,709 to Wells; British Patent No. 849,433 to Woolston; and International Patent No. WO93/08787. All of these patents are herein incorporated by reference in their entireties.

Another silicone material that can be especially useful in the silicone conditioning agents is insoluble silicone gum. The term "silicone gum," as used herein, means polyorganosiloxane materials having a viscosity at 25° C. of greater than or equal to 1,000,000 centistokes. Silicone gums are described by Petrarch and others including U.S. Pat. No. 4,152,416 to Spitzer et al. The "silicone gums" will typically, have a mass molecular weight in excess of about 200,000, generally between about 200,000 and about 1,000,000. Specific examples include polydimethylsiloxane, (polydimethyl siloxane) (methylvinylsiloxane) copolymer, poly(dimethyl siloxane) (diphenyl siloxane) (methylvinylsiloxane) copolymer, and mixtures thereof.

Typically, the silicone conditioning agent comprises a mixture of a polydimethylsiloxane gum, having a viscosity greater than about 1,000,000 centistokes and polydimethyl siloxane fluid having a viscosity of from about 10 centistokes to about 100,000 centistokes, wherein the ratio of gum to fluid is from about 30:70 to about 70:30, typically, from about 40:60 to about 60:40.

Another optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin.

In general, silicone materials which have a sufficient level of trifunctional and tetrafunctional siloxane monomer units (and hence, a sufficient level of crosslinking) such that they dry down to a rigid or hard film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Typically, the ratio of oxygen to silicon atoms is at least about 1.2:1.0 Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Examples of the more preferred optional silicones used include dimethicone, cyclomethicone, trimethyl silyl amodimethicone, phenyl trimethicone, trimethyl siloxy silicate, polyorganosiloxane, polyalkylsiloxane, polyarylsiloxane, polyalkylarylsiloxane, and polyestersiloxane copolymers.

The keratin treating compositions of the present invention are typically, liquids, which typically, are pourable at room temperature. The compositions hereof will comprise an aqueous carrier, i.e., water, which will generally be present at a level of about 20% to about 95% by weight of the composition, typically, from about 60% to about 85% for pourable, liquid formulations, such as shampoos, shower gels, liquid hand-soaps, and lotions. The compositions of the present invention can also be in other forms, such as gels, mousse, etc. In such cases, appropriate components known in the art, such as gelling agents (e.g., hydroxyethyl cellulose), etc. can be included in the compositions. Gels will typically, contain from about 20% to about 90% water. Mousses will be a low viscosity composition and will be packaged as a sprayable liquid according to techniques well known in the art, typically, in an aerosol canister including a propellant or a means for generating an aerosol spray.

The present keratin treating compositions may also comprise a variety non-essential, optional components suitable for rendering such compositions more cosmetically or aesthetically acceptable or to provide them with additional usage benefits. A variety of such are known to those skilled in the art in hair, skin, and nail care. These ingredients are well-known and include without limiting the invention thereto: pearlescent aids, such as coated mica, ethylene glycol distearate; opacifiers, such as Tin, preservatives, such as 1,2-dibromo-2,4-dicyano butane (MERGUARD® Nalco Chemical Company, Naperville, Ill., USA), benzyl alcohol, 1,3-bis(hydroxymethyl)-5, 5-dimethyl-2,3-imidazolidinedione (e.g., GLYDANT®, Lonza Inc., Fairlawn, N.J., USA), methylchloroisothiazolinone (e.g., KATHON®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetra-acetate (EDTA).

Another optional ingredient that can be advantageously used is an anti-static agent. The anti-static agent should not unduly interfere with the in-use performance and end-benefits of the composition. This is more important for shampoo compositions, and the anti-static agent should particularly not interfere with the anionic detersive surfactant. Suitable anti-static agents include, for example, tricetyl methyl ammonium chloride.

Typically, from about 0.1% to about 5% of such anti-static agent is incorporated into the shampoo compositions.

Though the polymer components may act to thicken the present compositions to some degree, the present compositions may also optionally contain other thickeners and viscosity modifiers, such as an ethanolamide of a long chain fatty acid, such as polyethylene (3) glycol lauramide and coconut monoethanolamide (cocamide MEA), ammonium xylene sulfonate, xanthan gum, and hydroxyethyl cellulose.

These optional components generally are used individually in the compositions of the present invention at a level of from about 0.01% to about 10%, typically, from about 0.05% to about 5.0% of the composition.

The compositions of the present invention are utilized conventionally, i.e., the hair or skin is shampooed or washed by applying an effective amount of the composition to the scalp or skin, and then rinsing it off with water. Application of the shampoo to the scalp in general, encompasses messaging or working the shampoo in the hair such that all or most of the hair on the scalp is contacted. The term an "effective amount" as used herein, is an amount which is effective in cleaning and conditioning the keratin substrate. Generally, from about 1 g to about 20 g of the composition is applied for cleaning and conditioning the keratin substrate, typically, the cosmetically acceptable medium is applied to keratin in a wet or damp state.

The compositions hereof can also be useful for cleaning and conditioning the skin. For such applications, the composition would be applied to the skin in a conventional manner, such as by rubbing or massaging the skin with the composition, optionally in the presence of water, and then rinsing it away with water. In the case of non-rinse-off products, the composition is left in full concentration in contact with the skin.

Another preferred embodiment consists of use in the form of a rinsing lotion to be applied mainly before or after shampooing. These lotions are typically, aqueous or aqueous-alcoholic solutions, emulsions, thickened lotions, or gels. If the compositions are presented in the form of an emulsion, they can be nonionic, anionic, or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic, and cellulose derivatives, and it is also possible to achieve thickening by means of a mixture of polyethylene glycol stearate or distearate or by means of a mixture of a phosphoric acid ester and an amide. The concentration of thickener is generally 0.05 to 15% by weight. If the compositions are presented in the form of a styling lotion, shaping lotion, or setting lotion, they generally comprise, in aqueous, alcoholic, or aqueous-alcoholic solution, the interjacent complexes defined above.

If the compositions of the instant invention are intended for use in the dyeing of keratin fibers, and in particular, human hair, they generally contain at least one oxidation dyestuff precursor and/or one direct dyestuff, in addition to the present interjacent complexes. They can also contain any other adjuvant normally used in this type of composition.

The pH of the dyeing compositions is generally 7 to 11 and can be adjusted to the desired value by adding an alkalizing agent.

The compositions according to the present invention can also be used for waving or straightening the hair. In this case, the composition generally contains, in addition to the instant interjacent complexes, one or more reducing agents and, if appropriate, other adjuvants normally used in this type of composition; such compositions are intended for use conjointly with a neutralizing composition.

In an embodiment of the present invention, an effective amount of the present water-soluble interjacent complex is added to an anionic surfactant-containing hair or skin care product, a cosmetically acceptable formulation. Thus, the water-soluble interjacent complexes compositions of the present invention can be used in, inter alia, shampoos, conditioners, shower gels, bar soaps, rinses, coloring products, bleaching products, setting lotions, blow-drying lotions, restructuring lotions, skin cleaners, skin care lotions, skin care creams, perms, and straightening products.

The present invention will further be described by reference to the following examples. The following examples are merely illustrative of the invention and are not intended to be limiting. Unless otherwise indicated, all percentages are by weight.

EXAMPLE 1

The ingredients in Table 1 were added to a 2-Liter Resin Kettle fitted with a condenser, stirrer, and thermocouple.

TABLE 1

| Ingredient | Charge (g) |
| --- | --- |
| Charge 1 | |
| Polyquaternium-7[1] | 237.3 |
| DADMAC[2] | 1076.9 |
| NaEDTA[3] | 0.75 |
| Charge 2 | |
| Sodium Persulfate | 4.1 |
| Deionized water | 25.4 |
| Charge 3 | |
| Deionized water | 409.7 |

[1]20 wt % aqueous gel available as in-process WSPQ7 from WSP Chemicals & Technologies, Inc., Ambridge, Pa.

TABLE 1-continued

| Ingredient | Charge (g) |
| --- | --- |

[2]64.8 wt. % solution in water available from Pearl River Polymer, Slidell, La.
[3]Tetrasodium N, N', N", N"' - ethylene diamine tetra acetic acid Charge 1 was added to the Resin Kettle and heated to 80° C. with stirring until homogeneous (about 2 hours). Approximate concentration of DADMAC was 53.0% and Polyquatemium-7 is 3.6% by weight. Charge 2 was fed to the Resin Kettle at a rate of 0.064 ml/min for a period of 50 minutes. After about a 12 minutes the temperature of the solution began to rise indicating that polymerization had begun. The feed rate of charge 1 was decreased to 0.16 ml/min for a period of 20 minutes. The temperature of the reaction mix increased to about 110° C. and was maintained there due to reflux. The remainder of charge 1 was fed to the Resin Kettle at a rate of 0.32 ml/min (about 50–60 minutes). The temperature was maintained between 100–105° C. Charge 3 was heated to at least 80° C., and maintained at this temperature with stirring for 40 minutes until a uniform mixture was formed. The solution was cooled to about 40° C. and 50 wt. % aqueous sodium hydroxide was added dropwise until the pH was between 6–7. The resulting solution contained 39.7% poly(DADMAC) and 2.7% Polyquatemium-7. The solution remained uniform after standing at room temperature for three months. A 5 wt. % aqueous solution (active polymer basis) of the poly (DADMAC)-Polyquatemium-7 interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 2

The ingredients in Table 2 were added to a 2-Liter Resin Kettle fitted with a condenser, stirrer, thermocouple and nitrogen purge tube.

TABLE 2

| Ingredient | Charge (g) |
| --- | --- |
| Charge 1 | |
| Polyquaternium-11[4] | 240.1 |
| MEHQ[5] | 0.0016 |
| Deionized water | 227.6 |
| Charge 2 | |
| Acrylamide (50%) | 82.4 |
| DADMAC (64.8%) | 44.9 |
| NaEDTA | 0.28 |
| Charge 3 | |
| 2,2'-Azobis(2-methylpropionamide)dihydrochloride[6] | 0.2 |
| Deionized water | 5.0 |
| Charge 4 | |
| Deionized water | 130.0 |
| Sodium metabisulfite | 2.0 |

[4]20 wt % aqueous solution available as Gafquat ® 755N from International Specialty Products, Wayne, New Jersey.
[5]Methyl ester of hydroquinone.
[6]Available as V-50 from Wako Chemicals USA, Inc., Dallas, Texas.

Charge 1 was added to the Resin Kettle with mixing, heat was applied to aid in homogenizing the solution. Charge 2 was added to the Resin Kettle, heating was continued with stirring and a nitrogen sub-surface purge at about 3–5 scfh was started. Heating was continued to 60° C. and the nitrogen purge was maintained for at least 30 minutes. Charge 3 was added to the Resin Kettle. An exotherm was noticed after one or two minutes after which time the nitrogen purge was reduced to a blanket headspace flow of about 0.5 scfh. The reaction temperature peaked at about 75° C. The temperature was maintained for about two hours at which time charge 4 was added to the Resin Kettle with stirring and held at 75° C. for 30 minutes. The solution remained uniform after standing at room temperature for three months. A 5 wt. % aqueous solution (active polymer basis) of the Polyquatemium-11-acrylamide/DADMAC copolymer interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 3

The ingredients in Table 3 were added to a 2-Liter Resin Kettle fitted with a condenser, stirrer, thermocouple and nitrogen purge tube

TABLE 3

| Ingredient | Charge (g) |
|---|---|
| Charge 1 | |
| Polyquaternium-28[7] | 156.7 |
| Deionized water | 97.4 |
| Charge 2 | |
| Sodium Hydroxide (50%) | 5.0 |
| 2-Acrylamido-2-methyl-2-propanesulfonic acid | 12.9 |
| Acrylic acid | 15.3 |
| Sodium Hydroxide (50%) | 11.7 |
| Acrylamide (50%) | 19.1 |
| Acryloyloxyethyl, trimethyl ammonium chloride (80.5%) | 70.3 |
| NaEDTA | 0.3 |
| Charge 3 | |
| Sodium persulfate | 0.2 |
| Deionized water | 6.0 |
| Charge 4 | |
| Deionized water | 6.0 |
| Sodium metabisulfite | 0.6 |
| Charge 5 | |
| Deionized water | 150.0 |
| Sodium metabisulfite | 1.5 |

[7]20 wt % aq. solution available as Gafquat ® HS-100 from International Specialty Products, Wayne, New Jersey.

Charge 1 was added to the Resin Kettle and mixed until uniform. Charge 2 was then added to the Resin Kettle an mixed until uniform. The pH should of the solution was about 5.1. The mixture was stirred with heating and a nitrogen sub-surface purge at about 3–5 scfh was begun for about 30 minutes. Charge 3 was added to the Resin Kettle wile stirring and about two minutes thereafter Charge 4 was added to the Resin Kettle.

In about two minutes, the solution temperature began to rise. After about three minutes, the nitrogen purge was reduced to a blanket headspace flow at about 0.5 scfh and the reaction temperature exceeded 80° C. After about one hour, charge 5 was added to the Resin Kettle, maintaining the temperature at 80° C. for at least 30 minutes. The solution remained uniform after standing at room temperature for three months. A 5 wt. % aqueous solution (active polymer basis) of the acrylic acid/AMPSA/acrylamide/AETAC copolymer—Polyquatemium-28 interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 4

A interjacent complex was prepared as in example 2 using the ingredients outlined in Table 4.

TABLE 4

| Ingredient | Charge (g) |
|---|---|
| Charge 1 | |
| Polyquaternium-10[8] | 35.1 |
| MEHQ | 0.0016 |
| Deionized water | 390.2 |
| Charge 2 | |
| Acrylamide (50%) | 20.4 |
| DADMAC (64.8%) | 30.6 |
| NaEDTA | 0.02 |
| Charge 3 | |
| 2,2'-Azobis(2-methylpropionamide)dihydrochloride | 0.4 |
| Deionized water | 7.5 |
| Charge 4 | |
| Deionized water | 250.0 |

[8]Dry product available as Celquat ® SC-230M from National Starch and Chemical, Bridgewater, New Jersey.

The resulting interjacent complex solution contained 4.7% Polyquatemium-10 and 4.0% acrylamide-DADMAC copolymer. The solution had a Brookfield viscosity of 122,000 cps measured using RV spindle No. 7@10 rpm at 25° C. The solution remained uniform after standing at room temperature for three months. A 5 wt. % aqueous solution (active polymer basis) of the acrylamide/DADMAC copolymer-Polyquaternium-10 interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 5

A 50/25/25 w/w DADMAC/acrylamide/acrylic acid terpolymer (Polyquaternium-39) was prepared using the ingredients in Table 5 and the polymerization procedure of example 3.

TABLE 5

| Ingredient | Charge (g) |
|---|---|
| Charge 1 | |
| DADMAC (64.8%) | 92.4 |
| Acrylic acid | 31.7 |
| Sodium Hydroxide (50%) | 4.6 |

TABLE 5-continued

| Ingredient | Charge (g) |
|---|---|
| acrylamide (50%) | 61.2 |
| Deionized water | 418.3 |
| NaEDTA | 0.03 |
| Charge 2 | |
| Sodium persulfate | 0.14 |
| Deionized water | 4.2 |
| Charge 3 | |
| Deionized water | 2.4 |
| Sodium metabisulfite | 0.02 |

The resulting polymer gel contained 19.8% polymer by weight. The terpolymer was used to make a interjacent complex using the polymerization method of example 3 and the ingredients listed in Table 6.

TABLE 6

| Ingredient | Charge (g) |
|---|---|
| Charge 1 | |
| Terpolymer described in Table 5 (19.8%) | 242.8 |
| Charge 2 | |
| Acrylamide (50%) | 60.5 |
| DADMAC (64.8%) | 46.5 |
| NaEDTA | 0.03 |
| Charge 3 | |
| Sodium persulfate | 0.9 |
| Deionized water | 4.7 |
| Charge 4 | |
| Deionized water | 3.9 |
| Sodium metabisulfite | 0.02 |
| Charge 5 | |
| Deionized water | 390.0 |
| Sodium metabisulfite | 4.2 |

The resulting interjacent complex solution contained 6.3% of the terpolymer described in Table 5 and 7.9% of the acrylamide-DADMAC copolymer. The solution remained uniform after standing at room temperature for three months. A 5 wt. % aqueous solution (active polymer basis) of the acrylamide/DADMAC copolymer-Polyquatemium-39 interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 6

A interjacent complex was prepared using the polymerization method described in example 2 and the ingredients in Table 7.

TABLE 7

| Ingredient | Charge (g) |
|---|---|
| Charge 1 | |
| Guar[9] | 5.0 |
| MEHQ[5] | 0.0016 |

TABLE 7-continued

| Ingredient | Charge (g) |
|---|---|
| Deionized water | 455.2 |
| Charge 2 | |
| Acrylamide (50%) | 51.8 |
| Acryloyloxyethyl, trimethyl ammonium chloride (80.5%) | 67.3 |
| NaEDTA | 0.16 |
| Charge 3 | |
| 2,2'-Azobis(2-methylpropionamide)dihydrochloride[6] | 0.25 |
| Deionized water | 6.0 |
| Charge 4 | |
| Deionized water | 100.0 |
| Sodium metabisulfite | 1.0 |

[9]WG-22 available from PolyPro, Inc., Dalton, Georgia.

The resulting interjacent complex solution contained 0.8% guar and 11.9% acrylamide-acryloyloxyethyl, trimethyl ammonium chloride copolymer. The solution remained uniform after standing at room temperature for three months. A 5 wt. % aqueous solution (active polymer basis) of the acrylamide/AETAC copolymer-guar interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLE 7

A interjacent complex was prepared using the polymerization method described in example 2 and the ingredients in Table 8.

TABLE 8

| Ingredient | Charge (g) |
|---|---|
| Charge 1 | |
| Xanthan gum[10] | 2.6 |
| MEHQ | 0.0016 |
| Deionized water | 457.6 |
| Charge 2 | |
| Acrylamide (50%) | 25.1 |
| Acryloyloxyethyl, trimethyl ammonium chloride (80.5%) | 65.7 |
| NaEDTA | 0.04 |
| Charge 3 | |
| 2,2'-Azobis(2-methylpropionamide) dihydrochloride[6] | 0.25 |
| Deionized water | 3.4 |
| Charge 4 | |
| Deionized water | 150.0 |
| Sodium metabisulfite | 0.5 |

[10]Flo-Vis-Plus, MI Drilling Fluids, Houston, Texas.

The resulting interjacent complex solution contained 0.5% xanthan gum and 12.0% acrylamide-acryloyloxyethyl, trimethyl ammonium chloride copolymer. The solution remained uniform after standing at room temperature for three months. A 5 wt. % aqueous solution (active polymer basis) of the acrylamide/AETAC copolymer-xanthan gum interjacent complex passed through a 100 mesh sieve (EW-59994-16, Cole-Parmer Instrument Company, Vernon Hills, Ill.) and left no insoluble polymer residue on the screen. A 2.5 wt. % solution was also measured for turbidity on a standard laboratory turbidimeter (Model 2100AN, Loveland, Colo.) and measured less than 20 ntu.

EXAMPLES 8–14

The following physical blends of the polymers in Table 9 were prepared by adding 1:1 weight ratios of the respective polymer solutions to a suitable vessel equipped with an overhead mixer and mixing the solution until uniform.

TABLE 9

| Example No. | Polymer 1 | Polymer 2 |
|---|---|---|
| 8 | Polyquaternium-7[1] | Polyquaternium-6[11] |
| 9 | Polyquaternium-11[4] | Polyquaternium-7[1] |
| 10 | Polyquaternium-28[7] | AMPS-acrylic acid-acrylamide-AETAC copolymer[12] |
| 11 | 10% aqueous solution of Polyquaternium-10[8] | Polyquaternium-7[13] |
| 12 | Polyquaternium-39[14] | Polyquaternium-7[15] |
| 13 | 2% aqueous solution of guar | Polyquaternium-33[16] |
| 14 | 1% aqueous solution of xanthan gum | Polyquaternium-33[17] |

[1]WSPQ7 available from WSP Chemicals & Technologies, Inc., Ambridge, Pennsylvania.
[4]20 wt % aqueous solution available as Gafquat ® 755N from International Specialty Products, Wayne, New Jersey.
[7]20 wt % aqueous solution available as Gafquat ® HS-100 from International Specialty Products, Wayne, New Jersey.
[8]Dry product available as Celquat ® SC-230M from National Starch and Chemical, Bridgewater, New Jersey.
[11]Prepared as described in Example 1 without Polyquaternium-7 being present.
[12]Prepared as described in Example 3 without Polyquaternium-28 being present.
[13]Prepared as described in Example 4 without Polyquaternium-10 being present.
[14]Prepared as described in Example 5, Table 5.
[15]Prepared as described in Example 5, Table 6 without the polymer in Table 5 being present.
[16]Prepared as described in Example 6 without guar being present.
[17]Prepared as described in Example 7 without xanthan gum being present.

The solutions were allowed to stand at room temperature. After about 3 to 4 weeks, all of the solutions prepared in example 8–14 had formed two visibly distinct layers, i.e. they began to separate into two phases.

EXAMPLES 15–22

A shampoo was prepared by sequentially adding the ingredients in Table 10 to a suitable container with mixing.

TABLE 10

(all entries in grams)

| Example No. | 15 | 16 | 17 | 18 | 19 | 20 | 21 | 22 |
|---|---|---|---|---|---|---|---|---|
| Deionized water | 67.4 | 67.4 | 67.4 | 67.4 | 67.4 | 67.4 | 67.4 | 67.4 |
| Sodium lauryl sulfate (70%) | 17.0 | 17.0 | 17.0 | 17.0 | 17.0 | 17.0 | 17.0 | 17.0 |
| Sodium laureth sulfate | 0.5 | 0.5 | 0.5 | 0.5 | 0.5 | 0.5 | 0.5 | 0.5 |
| Cocamidopropyl betaine | 6.0 | 6.0 | 6.0 | 6.0 | 6.0 | 6.0 | 6.0 | 6.0 |
| Coconut diethanolamide | 2.5 | 2.5 | 2.5 | 2.5 | 2.5 | 2.5 | 2.5 | 2.5 |
| Sodium PCA[18] | 1.0 | 1.0 | 1.0 | 1.0 | 1.0 | 1.0 | 1.0 | 1.0 |
| Interjacent complex of example 1 | | 2.0 | | | | | | |
| Interjacent complex of example 2 | | | 4.0 | | | | | |
| Interjacent complex of example 3 | | | | 4.0 | | | | |
| Interjacent complex of example 4 | | | | | 4.5 | | | |
| Interjacent complex of example 5 | | | | | | 4.0 | | |
| Interjacent complex of example 6 | | | | | | | 2.0 | |
| Interjacent complex of example 7 | | | | | | | | 2.0 |
| Sodium chloride | 2.0 | 2.0 | 2.0 | 2.0 | 2.0 | 2.0 | 2.0 | 2.0 |

[18]Available from Minaloa Skin Care Products, Irvine, California.

The shampoos of examples 15–22 were used to clean human hair and were all able to adequately cleanse the hair. However, while examples 16–22 also provided excellent wet combing and dry combing properties, the shampoo of example 15 left the hair more difficult to comb due to tangling and more prone to static flyaway when the hair was dry.

EXAMPLES 23–25

An oil-based hand cream was prepared using the ingredients listed in Table 11.

TABLE 11

| Ingredients | Example 23 (g) | Example 24 (g) | Example 25 (g) |
|---|---|---|---|
| Skin care additive[19] | 2.0 | 2.0 | 2.0 |
| Skin care additive[20] | 2.0 | 2.0 | 2.0 |
| Skin care additive[21] | 4.0 | 4.0 | 4.0 |
| Skin care additive[22] | 3.0 | 3.0 | 3.0 |
| Mineral oil | 2.0 | 2.0 | 2.0 |
| $C_{16}$–$C_{18}$ alcohols | 1.7 | 1.7 | 1.7 |
| Lanolin | 1.5 | 1.5 | 1.5 |
| Propylene glycol | 5.0 | 5.0 | 5.0 |
| Deionized water | 78.6 | 78.6 | 78.6 |
| Interjacent complex of example 2 | | 2.0 | |
| Interjacent complex of example 1 | | | 2.0 |

TABLE 11-continued

| Ingredients | Example 23 (g) | Example 24 (g) | Example 25 (g) |
|---|---|---|---|

[19]available as A6 from Manhoko Ltd., Hong Kong, China.
[20]available as A25 from Manhoko Ltd., Hong Kong, China.
[21]available as IPM from Manhoko Ltd., Hong Kong, China.
[22]available as OP from Manhoko Ltd., Hong Kong, China.

The creams of examples 23, 24 and 25 were applied to human hands. The hands felt softer and less dry after application of the cremes in examples 24 and 25 than with the cream of example 23.

The present invention has been described with reference to specific details of particular embodiments thereof. It is not intended that such details be regarded as limitations upon the scope of the invention except insofar as and to the extent that they are included in the accompanying claims.

We claim:

1. A composition for treating a keratin based substrate comprising a cosmetically acceptable medium containing a water-soluble interjacent complex comprised of:
   (a) a water-soluble host polymer selected from the group consisting of water-soluble poly(meth)acrylates, water-soluble polyamides, water-soluble polyesters, water-soluble polyurethanes, water-soluble poly(vinyl amine), water-soluble poly(ethylene imine), water-soluble amine/epihalohydrin polyamines, water-soluble poly(meth)acrylamide, water-soluble (meth) acrylamide copolymers, water-soluble poly(meth) acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth) acrylamidopropyltrimethyl ammonium halides, copolymers of (meth)acrylamidopropyltrimethyl ammonium halides, poly(meth) acryloyloxyethyltrimethyl ammonium halides, copolymers of (meth)acryloyloxyethyltrimethyl ammonium halides, poly(meth)acryloyloxyethyltrimethyl ammonium methyl sulfate, copolymers of (meth) acryloyloxyethyltrimethyl ammonium methyl sulfate, xanthan gums, sodium alginates, galactomanans, carageenan, gum arabic, hydroxyethyl cellulose, hydroxypropyl cellulose, diallyl dimethyl ammonium chloride graft copolymers of hydroxyethylcellulose, polymeric quaternary ammonium salts of hydroxyethyl celluloses reacted with a trimethyl ammonium substituted epoxide, polymeric quaternary ammonium salts of hydroxyethyl celluloses reacted with lauryl dimethyl ammonium substituted epoxides, a quaternary ammonium derivative of hydroxypropyl guar and combinations thereof; and
   (b) one or more water-soluble monomers polymerized to form an intercalated polymer in the presence of the host polymer in (a), wherein the weight ratio of the host polymer to the intercalated polymer is from 1:100 to 100:1, and the resulting water-soluble interjacent complex forms a solution in water that is free of insoluble polymer particles and maintains one uniform phase after standing at ambient conditions for at least three months.

2. The keratin treating composition of claim 1 further comprising 5% to 50%, by weight, of a surfactant component selected from the group consisting of anionic surfactants, amphoteric surfactants, cationic surfactants, nonionic surfactants, and zwitterionic surfactants.

3. The keratin treating composition of claim 2, wherein the anionic surfactant is one or more selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, disodium N-octadecyl sulfofosuccinanrate, tetrasodium N-(1,2-dicarboxyethyl)-N-octadecylsulfosuccinamate, diamyl ester of sodium sulfosuccinic acid, dihexyl ester of sodium sulfosuccinic acid, and dioctyl esters of sodium sulfosuccinic acid.

4. The keratin treating composition of claim 2, wherein the amphoteric surfactant is one or more selected from the group consisting of sodium 3-dodecyl-aminopropionate, sodium 3-dodecylaminopropane sulfonate, sodium lauryl sarcosinate, and N-alkyltaurines.

5. The keratin treating composition of claim 2, wherein the zwitterionic surfactant is one or more selected from the group consisting of coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, amidobetaines, and amidosulfobetaines.

6. The keratin treating composition of claim 1 further comprising a silicone conditioning agent.

7. The keratin treating composition of claim 1 further comprising an organic water insoluble liquid selected from the group consisting of hydrocarbon oils, fatty esters having 10 to 22 carbon atoms, and mixtures thereof.

8. The keratin treating composition of claim 1, wherein the molecular weight of the polymer in (a) and the polymer in (b) in the interjacent complex are each at least 1,000.

9. The keratin treating composition of claim 1, wherein the water-soluble host polymer is one or more selected from the group consisting of water-soluble poly(meth)acrylates, water-soluble polyamides, water-soluble polyesters, water-soluble polyurethanes, water-soluble poly (vinyl amine), water-soluble poly(ethylene imine), water-soluble amine/epihalohydrin polyamines, water-soluble poly(meth) acrylamide, water-soluble (meth)acrylamide copolymers, water-soluble poly(meth)acrylic acid, water-soluble copolymers of (meth)acrylic acid, poly(diallyl dimethyl ammonium halides), copolymers of diallyl dimethyl ammonium halides, water-soluble vinyl pyrrolidone, water-soluble copolymers of vinyl pyrrolidone, poly(meth) acrylamidopropyltrimethyl ammonium halides, copolymers of (meth)acrylamidopropyltrimethyl ammonium halides, poly(meth)acryloyloxyethyltrimethyl ammonium halides, copolymers of (meth)acryloyloxyethyltrimethyl ammonium halides, poly(meth)acryloyloxyethyltrimethyl ammonium methyl sulfate, and copolymers of (meth)acryloyloxyethyltrimethyl ammonium methyl sulfate.

10. The keratin treating composition of claim 1, wherein the water-soluble host polymer is one or more selected from the group consisting of xanthan gums, sodium alginates, galactomanans, carageenan, and gum arabic.

11. The keratin treating composition of claim 1, wherein the host polymer is one or more selected from the group consisting of hydroxyethyl cellulose, hydroxypropyl cellulose, diallyl dimethyl ammonium chloride graft copolymers of hydroxyethylcellulose, polymeric quaternary ammonium salts of hydroxyethyl celluloses reacted with a trimethyl ammonium substituted epoxide, and polymeric quaternary ammonium salts of hydroxyethyl celluloses reacted with lauryl dimethyl ammonium substituted epoxides.

12. The keratin treating composition of claim 1, wherein the water-soluble host polymer is a quaternary ammonium derivative of hydroxypropyl guar.

13. The keratin treating composition of claim 1, wherein the monomers in (b) comprise a monomer mix comprised of (i) 0 to 100 mol % of one or more cationic monomers; (ii) 0 to 100 mol % of one or more anionic monomers; and (iii) 0 to 100 mol % of one or more nonionic monomers, wherein the sum of (i), (ii), and (iii) is 100 mol %.

14. The keratin treating composition of claim 13, wherein the cationic monomer (i) is one or more selected from the group consisting of (meth)acrylamidopropyltrimethyl ammonium halides, (meth)acryloyloxyethyltrimethyl ammonium halides, poly(meth)acryloyloxyethyltrimethyl ammonium methyl sulfate, and diallyl dimethyl ammonium halides.

15. The keratin treating composition of claim 13, wherein the anionic monomer (ii) comprises one or more sulfonic acid containing monomers selected from the group consisting of 2-acrylamido-2-methylpropane sulfonic acid, 2-methacrylamido-2-methylpropane sulfonic acid, sulfonated styrene, vinyl sulfonic acids, and allyl ether sulfonic acids.

16. The keratin treating composition of claim 15, wherein the mol ratio of cationic monomer (i) to sulfonic acid containing anionic monomer (ii) ranges from 20:80 to 95:5.

17. The keratin treating composition of claim 13, wherein the anionic monomer (ii) comprises one or more carboxylic acid containing monomers selected from the group consisting of (meth)acrylic acid, maleic acid, itaconic acid, N-(meth)acrylamidopropyl, N,N-dimethyl,amino acetic acid, N-(meth)acryloyloxyethyl, N,N-dimethyl,amino acetic acid, N-(meth)acryloyloxyethyl, N,N-dimethyl,amino acetic acid, crotonic acid, (meth)acrylamidoglycolic acid, and 2-(meth)acrylamido-2-methylbutanoic acid.

18. The keratin treating composition of claim 17, wherein the mol ratio of cationic monomer (i) to carboxylic acid containing anionic monomer (ii) ranges from 20:80 to 95:5.

19. The keratin treating composition of claim 13, wherein the nonionic monomer (iii) comprises one or more selected from the group consisting of $C_1$–$C_{22}$ straight or branched chain alkyl or aryl (meth)acrylates, $C_1$–$C_{22}$ straight or branched chain N-alkyl or aryl (meth)acrylamide, (meth)acrylamide, N-methyl(meth)acrylamide, N-vinylpyrrolidone, vinyl acetate, ethoxylated (meth)acrylates, propoxylated (meth)acrylates, hydroxy functional (meth)acrylates, N,N-dimethyl(meth)acrylamide, styrene, $C_1$–$C_{22}$ straight or branched chain alkyl allyl ethers, and $C_1$–$C_{22}$ aryl allyl ethers.

20. The keratin treating composition of claim 13, wherein the monomer mix in (b) further comprises (iv) a branching quantity of one or more monomers that have two or more sites of reactive unsaturation.

21. The keratin treating composition of claim 20, wherein the monomers having two or more sites of reactive unsaturation (iv) are selected from the group consisting of ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth)acrylate, pentaerythritol di(meth)acrylate, pentaerythritol tri(meth)acrylate, pentaerythritol tetra(meth)acrylate, glycerol di(meth)acrylate, glycerol allyloxy di(meth)acrylate, 1,1,1-tris(hydroxymethyl)ethane di(meth)acrylate, 1,1,1-tris(hydroxymethyl)ethane tri(meth)acrylate, 1,1,1-tris(hydroxymethyl)propane di(meth)acrylate, 1,1,1-tris(hydroxymethyl)propane tri(meth)acrylate, triallyl cyanurate, triallyl isocyanurate, triallyl trimellitate, diallyl phthalate, diallyl terephthalte, divinyl benzene, triallylamine, and methylenebis (meth) acrylamide.

22. The keratin treating composition of claim 20, wherein the monomers having two or more sites of reactive unsaturation are present at 0.0001 to 0.1 mol % based on the total number of mols of (i), (ii), and (iii).

23. The keratin treating composition of claim 1, wherein the reduced viscosity of the interjacent complex, as determined in a Ubbelhhde Capillary Viscometer at 0.05% by weight concentration of polymer in 1M NaCl solution, at 30° C., pH 7 ranges from 0.1 to 20 dl/g.

24. The keratin treating composition of claim 1, wherein the interjacent complex is prepared by solution polymerization.

25. The keratin treating composition of claim 1, wherein the interjacent complex is prepared as a water-in-oil emulsion.

26. The keratin treating composition of claim 1, wherein the cosmetically acceptable medium is selected from the group consisting of an aftershave, a sunscreen, a hand lotion, a liquid soap, a bar soap, a bath oil bar, a shaving cream, a dishwashing liquid, a conditioner, a hair dye, a permanent wave, a hair relaxer, a hair bleach, a hair setting composition, a styling gel, or a shower gel.

27. The keratin treating composition of claim 1, wherein the keratin based substrate is selected from human hair, human skin, and human nails.

* * * * *